(12) United States Patent
Dierker et al.

(10) Patent No.: US 8,894,983 B2
(45) Date of Patent: Nov. 25, 2014

(54) CONDITIONER AND CONDITIONING SHAMPOO COMPOUND CONTAINING PENTAERYTHRITOL ESTER

(75) Inventors: Markus Dierker, Düsseldorf (DE); Hans-Martin Haake, Erkrath (DE); Daniela Prinz, Dormagen (DE); Junko Kano, Tokyo (JP); Kakushi Doki, Tokyo (JP); Tae-Seong Kim, Gyeonggi (KR); Koichi Masaki, Ibaraki (JP); Sybille Cornelsen, Ratingen (DE)

(73) Assignee: Cognis IP Management GmbH, Duesseldorf (DE)

( * ) Notice: Subject to any disclaimer, the term of this patent is extended or adjusted under 35 U.S.C. 154(b) by 80 days.

(21) Appl. No.: 13/635,203

(22) PCT Filed: Mar. 5, 2011

(86) PCT No.: PCT/EP2011/001097
§ 371 (c)(1),
(2), (4) Date: Sep. 14, 2012

(87) PCT Pub. No.: WO2011/113536
PCT Pub. Date: Sep. 22, 2011

(65) Prior Publication Data
US 2013/0004449 A1    Jan. 3, 2013

(30) Foreign Application Priority Data
Mar. 16, 2010   (EP) .................................... 10002733

(51) Int. Cl.
| | | |
|---|---|---|
| *A61Q 5/12* | (2006.01) | |
| *A61K 8/00* | (2006.01) | |
| *A61K 8/37* | (2006.01) | |
| *A61K 8/891* | (2006.01) | |
| *A61K 8/898* | (2006.01) | |
| *A61Q 5/02* | (2006.01) | |

(52) U.S. Cl.
CPC .................. *A61K 8/375* (2013.01); *A61K 8/891* (2013.01); *A61K 8/898* (2013.01); *A61Q 5/02* (2013.01); *A61Q 5/12* (2013.01)
USPC ...................................... 424/70.12; 424/70.1

(58) Field of Classification Search
CPC combination set(s) only.
See application file for complete search history.

(56) References Cited

U.S. PATENT DOCUMENTS

2006/0079435 A1 *  4/2006  Bigorra Llosas et al. ...... 510/499
2008/0249192 A1 * 10/2008  Goget et al. ................... 514/786

FOREIGN PATENT DOCUMENTS

| EP | 1136066 A2 * | 9/2001 |
|---|---|---|
| EP | 1216685 | 6/2002 |
| EP | 1792604 | 6/2007 |
| EP | 2077139 | 7/2009 |
| JP | 2005336136 | 12/2005 |
| JP | 2005336136 A * | 12/2005 |
| WO | WO-99/13839 | 3/1999 |
| WO | WO 9913839 A1 * | 3/1999 |
| WO | WO-01/01949 | 1/2001 |
| WO | WO 0101949 A1 * | 1/2001 |
| WO | WO-2008/012442 | 1/2008 |
| WO | WO 2009083590 A1 * | 7/2009 |

OTHER PUBLICATIONS

Human translation of Derosier et al. WO 2009083590 A1(2009)—Table 1 only.*
Machine translation of Derosier et al. WO 2009083590 A1 (2009).*
Human translation of Derosier et al. WO 2009083590 A1 (2009)—Table 1 only.*

* cited by examiner

*Primary Examiner* — Sean Basquill
*Assistant Examiner* — Andrew S Rosenthal
(74) *Attorney, Agent, or Firm* — Servilla Whitney LLC

(57) ABSTRACT

The invention relates to a cosmetic preparation containing (a) esters of fatty acids having 6 to 12 carbon atoms with pentaerythritol and (b) silicones.

14 Claims, No Drawings

CONDITIONER AND CONDITIONING SHAMPOO COMPOUND CONTAINING PENTAERYTHRITOL ESTER

CROSS-REFERENCE TO RELATED APPLICATIONS

This application is the National Stage entry of PCT/EP2011/001097, filed on Mar. 5, 2011, which claims priority to European Patent application number 10002733.3, filed on Mar. 16, 2010, both of which are incorporated herein by reference in their entireties.

TECHNICAL FIELD

The invention is in the field of cosmetic conditioners and conditioning shampoo compositions which comprise silicones and certain esters of pentaerythritol.

BACKGROUND

Hair conditioners have always been used in order to improve the structure and appearance of hair. Hair treatments such as coloring or perming result in structural damage to the hair. The hair becomes brittle and matt, and the hair ends often split. In particular, after washing the hair, it is virtually impossible to comb the hair.

For this reason, cosmetic preparations have for a long time already been supplied which provide a remedy. Firstly, 2-in-1 shampoos, which act as shampoo with integrated conditioner, have existed for a long time on the market. Even during hair washing, the hair is conditioned, meaning that the hair can be combed directly very easily after rinsing. In addition, there are also hair rinses and hair treatments which are used separately after hair washing.

Favored ingredients for all of these applications are oils, such as natural and essential oils, silicone oils, fatty alcohols and quaternary ammonium compounds. In this connection, it has been found that it is of considerable importance to apply as much as possible of these components to the hair in order to attain a particularly good conditioning effect.

In one or more aspects, provided herein are conditioners which, as a result of deposition of large amounts of the oils used and in particular silicone oil, lead to improved conditioning of the hair.

SUMMARY

One aspect of the invention relates to a cosmetic preparation comprising: (a) esters of fatty acids having 4 to 12 carbon atoms with pentarythritol and (b) silicones. In one or more embodiments of the cosmetic preparation, the ester component comprises an ester of pentareythritol with caprylic acid and the silicone component comprises dimethicones or amodimethicones. In some embodiment, the cosmetic preparation further comprises quaternary ammonium compounds and/or waxes and oils.

DETAILED DESCRIPTION

Surprisingly, it has been found that the deposition of silicone oils on hair can be increased by the presence of fatty acid esters of pentaerythritol. The present invention therefore firstly provides a cosmetic preparation comprising
(a) esters of fatty acids having 4 to 12 carbon atoms with pentaerythritol and
(b) silicones.

Esters of Fatty Acids having 4 To 12 Carbon Atoms and Pentaerythritol

The esters can have a single type of fatty acid acyl groups or a mixture of different fatty acid acyl groups, the fatty acids can be branched or unbranched and/or saturated or unsaturated. However, preference is given to relatively short alkyl chains. It is to be assumed that more hydrophilic esters intensify the deposition of the silicones.

Preferably, therefore, linear or branched, saturated or unsaturated fatty acids with acyl groups having 4 to 12 carbon atoms are used for the esterification. Particular preference is given to acyl groups having 6 to 10 carbon atoms. As component (a), very particular preference is given to using an ester of pentaerythritol with caprylic acid.

To prepare this particularly preferred ester, 1 mol of pentaerythritol is reacted with 2 mol of caprylic acid, producing a diester as main component. In a preferred embodiment of the invention, these are esters of pentaerythritol with a fraction of 5-35% by weight of monoester, 20-50% by weight of diester and 20-50% by weight of triester, and optionally tetraester. Particular preference is given to a content of 10-25% by weight of monoester, 25-40% by weight of diester and 30-40% by weight of triester, and optionally tetraester and very particularly preferably 15-25% by weight of monoester, 30-40% by weight of diester, 25-35% by weight of triester and 5-11% by weight of tetraester. At the same time, it is thus ensured that the amount of the unreacted pentaerythritol remains very small (less than 0.5% by weight) and therefore transparent and light-permeable preparations can also be produced. The pentaerythritol esters that are to be used with preference are liquid since they thus have particularly good handling and can be formulated better. In the preparations according to the invention, the aforementioned pentaerythritol esters are used in amounts of from 0.01 to 5% by weight, preferably from 0.1 to 3% by weight and particularly preferably from 1 to 3% by weight.

Silicones

For conditioning hair, preference is given to using silicones in shampoos, hair rinses, hair treatments and the like. Suitable silicone compounds are, for example, dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds which can be present either in liquid form or in resin form at room temperature.

Within the context of the present invention, it has been found that it is particularly advantageous if dimethicones or amodimethicones are used as component (b).

Usually, the silicones are used here in amounts of from 0.01 to 5% by weight in the cosmetic preparations and preferably 1 to 2% by weight.

Cosmetic Preparations

The cosmetic preparations according to the invention can be present in the form of hair shampoos, hair lotions, hair rinses, hair treatments and the like. These compositions can also comprise, as further auxiliaries and additives, mild surfactants, oil bodies, emulsifiers, pearlescent waxes, consistency regulators, thickeners, superfatting agents, stabilizers, polymers, fats, waxes, lecithins, phospholipids, biogenic active ingredients, antioxidants, deodorants, antiperspirants, antidandruff agents, film formers, swelling agents, hydrotropes, solubilizers, preservatives, perfume oils, dyes and the like.

Surfactants

Shampoo preparations generally comprise as one of the main components surfactants for cleaning the hair. Surface-active substances which may be present are anionic, nonionic, cationic and/or amphoteric and/or zwitterionic surfactants, the fraction of which in the compositions is usually about 1 to 70, preferably 5 to 50 and in particular 10 to 30% by weight. Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxyl mixed ether sulfates, monoglyceride (ether)sulfates, fatty acid amide (ether)sulfates, mono- and dialkyl sulfosuccinates, mono- and dialkyl sulfosuccinamates, sulfotriglycerides, amide soaps, ethercarboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates and carboxylates, protein fatty acid condensates (in particular wheat-based vegetable products) and alkyl (ether)phosphates. If the anionic surfactants contain polyglycol ether chains, these can have a conventional homolog distribution, but preferably have a narrowed homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these can have a conventional homolog distribution, but preferably have a narrowed homolog distribution. Typical examples of cationic surfactants are quaternary ammonium compounds, such as, for example, dimethyldistearylammonium chloride, and ester quats, in particular quaternized fatty acid trialkanolamine ester salts. Typical examples of amphoteric and/or zwitterionic surfactants are alkylbetaines, alkylamidobetaines, aminopropionates, aminoglycinates, imidazoliniumbetaines and sulfobetaines. The specified surfactants are exclusively known compounds. Typical examples of particularly suitable mild, i.e. particularly skin-compatible surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ethercarboxylic acids, alkyl oligoglucosides, fatty acid glucamides, alkylamidobetaines, amphoacetals and/or protein fatty acid condensates, the latter preferably based on wheat proteins.

Oil Bodies

Besides the aforementioned silicones, the cosmetic preparations according to the invention can, however, also comprise yet further oil bodies. Oil bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols and/or esters of branched $C_6$-$C_{13}$-carboxylic acids with linear or branched $C_6$-$C_{22}$-fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxycarboxylic acids with linear or branched $C_6$-$C_{22}$-fatty alcohols, in particular dioctyl malate, esters of linear and/or branched fatty acids with polyhydric alcohols (such as e.g. propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as e.g. dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as e.g. dicaprylyl ether (Cetiol® OE), ring-opening products of epoxidized fatty acid esters with polyols and/or aliphatic or naphthenic hydrocarbons, like e.g. such as squalane, squalene or dialkylcyclohexanes.

Emulsifiers

Furthermore, the cosmetic preparations of the present invention, particularly if they are in the form of creams such as hair treatments, can comprise emulsifiers. Suitable emulsifiers are, for example, nonionogenic surfactants of at least one of the following groups:

Addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and alkylamines having 8 to 22 carbon atoms in the alkyl radical;

alkyl and/or alkenyl oligoglycosides having 8 to 22 carbon atoms in the alk(en)yl radical and ethoxylated analogs thereof;

addition products of from 1 to 15 mol of ethylene oxide onto castor oil and/or hydrogenated castor oil;

addition products of from 15 to 60 mol of ethylene oxide onto castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and adducts thereof with 1 to 30 mol of ethylene oxide;

partial esters of polyglycerol (average degree of self-condensation 2 to 8), polyethylene glycol (molecular weight 400 to 5000), trimethylolpropane, sugar alcohols (e.g. sorbitol), alkylglycosides (e.g. methylglucoside, butylglucoside, laurylglucoside), and polyglycosides (e.g. cellulose) with saturated and/or unsaturated, linear or branched fatty acids having 12 to 22 carbon atoms and/ or hydroxycarboxylic acids having 3 to 18 carbon atoms, and adducts thereof with 1 to 30 mol of ethylene oxide;

mixed esters of pentaerythritol, fatty acids, citric acid and fatty alcohol and/or mixed esters of fatty acids having 6 to 22 carbon atoms, methylglucose and polyols, preferably glycerol or polyglycerol, mono-, di- and trialkyl phosphates, and also mono-, di- and/or tri-PEG-alkyl phosphates and salts thereof;

wool wax alcohols;

polysiloxane-polyalkyl-polyether copolymers and corresponding derivatives;

block copolymers, e.g. polyethylene glycol-30 dipolyhydroxystearate;

polymer emulsifiers, e.g. Pemulen grades (TR-1,TR-2) from Goodrich;

polyalkylene glycols, glycerol carbonate, and ethylene oxide addition products.

The addition products of ethylene oxide and/or of propylene oxide onto fatty alcohols, fatty acids, alkylphenols or onto castor oil are known, commercially available products. These are homolog mixtures whose average degree of alkoxylation corresponds to the quantitative amounts of ethylene oxide and/or propylene oxide and substrate with which the addition reaction is carried out.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric diglyceride, malic acid monoglyceride, malic acid diglyceride, and technical-grade mixtures thereof which can also contain small amounts of triglyceride to a minor extent from the production process. Addition products of from 1 to 30, preferably 5 to 10, mol of ethylene oxide onto the specified partial glycerides are likewise suitable.

Sorbitan Esters

Sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Addition products of from 1 to 30, preferably 5 to 10, mol of ethylene oxide onto the specified sorbitan esters are likewise suitable.

Polyglycerol Esters

Typical examples of suitable polyglycerol esters are polyglyceryl-2 dipolyhydroxystearate (Dehymuls® PGPH), polyglycerol-3-diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Anionic Emulsifiers

Typical anionic emulsifiers are aliphatic fatty acids having 12 to 22 carbon atoms, such as, for example, palmitic acid, stearic acid or behenic acid, and also dicarboxylic acids having 12 to 22 carbon atoms, such as, for example, azelaic acid or sebacic acid.

Amphoteric and Cationic Emulsifiers

Furthermore, zwitterionic surfactants can be used as emulsifiers. Zwitterionic surfactants is the term used to refer to those surface-active compounds which carry at least one quaternary ammonium group and at least one carboxylate group and one sulfonate group in the molecule. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocosacylaminopropyldimethylammonium glycinate, and 2-alkyl-3-carb oxymethyl-3-hydroxyethylimidazolines having in each case 8 to 18 carbon atoms in the alkyl or acyl group, and cocoacylaminoethylhydroxyethyl carboxymethylglycinate. Particular preference is given to the fatty acid amide derivative known under the CTFA name Cocamidopropyl Betaine. Likewise suitable emulsifiers are ampholytic surfactants. Ampholytic surfactants are understood as meaning those surface-active compounds which, apart from a $C_{8/18}$-alkyl or acyl group in the molecule, contain at least one free amino group and at least one —COOH or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12/18}$-acylsarcosine. Finally, cationic surfactants are also suitable as emulsifiers, with those of the ester quat type, preferably methyl-quaternized difatty acid triethanolamine ester salts, being particularly preferred.

Fats and Waxes

Typical examples of fats are glycerides, i.e. solid or liquid vegetable or animal products which consist essentially of mixed glycerol esters of higher fatty acids; suitable waxes are inter alia natural waxes, such as e.g. candelilla wax, carnauba wax, Japan wax, espartograss wax, cork wax, guaruma wax, rice germ oil wax, sugarcane wax, ouricury wax, montan wax, beeswax, shellac wax, spermaceti, lanolin (wool wax), uropygeal grease, ceresin, ozokerite (earth wax), petrolatum, paraffin waxes, microwaxes; chemically modified waxes (hard waxes), such as e.g. montan ester waxes, sasol waxes, hydrogenated jojoba waxes, and synthetic waxes, such as e.g. polyalkylene waxes and polyethylene glycol waxes. As well as the fats, suitable additives are also fat-like substances, such as lecithins and phospholipids. The term lecithins is understood by the person skilled in the art as meaning those glycerophospholipids which are formed from fatty acids, glycerol, phosphoric acid and choline by esterification. Lecithins are therefore also often as phosphatidylcholines (PC) in the specialist field. Examples of natural lecithins which may be mentioned are the kephalins, which are also referred to as phosphatidic acids and are derivatives of 1,2-diacyl-sn-glycerol-3-phosphoric acids. By contrast, phospholipids are usually understood as meaning mono- and preferably diesters of phosphoric acid with glycerol (glycerol phosphates), which are generally included among the fats. In addition, sphingosines and/or sphingolipids are also suitable.

Pearlescent Waxes

Suitable pearlescent waxes are, for example: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have in total at least 24 carbon atoms, specifically laurone and distearyl ether; fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Consistency Regulators and Thickeners

Suitable consistency regulators are primarily fatty alcohols or hydroxyl fatty alcohols having 12 to 22 and preferably 16 to 18 carbon atoms and also partial glycerides, fatty acids or hydroxyl fatty acids. Preference is given to a combination of these substances with alkyl oligoglucosides and/or fatty acid-N-methylglucamides of identical chain length and/or polyglycerol poly-12-hydroxystearates. Suitable thickeners are, for example, Aerosil grades (hydrophilic silicas), poly-saccharides, in particular xanthan gum, guar guar, agar agar, alginates and tyloses, carboxyme-thylcellulose and hydroxy-ethyl- and hydroxypropylcellulose, also relatively high molecular weight polyethylene glycol mono- and diesters of fatty acids, polyacrylates, (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone. Bentonites, such as e.g. Bentone® Gel VS-5PC (Rheox), which is a mixture of cyclopentasiloxane, disteardimonium hectorite and propylenecarbonate, have also proven to be particularly effective. Also of suitability are surfactants such as, for example, ethoxylated fatty acid glycerides, esters of fatty acids with polyols, such as, for example, pentaerythritol or trimethylolpropane, fatty alcohol ethoxylates with a narrowed homolog distribution or alkyl oligoglucosides, and also electrolytes such as sodium chloride and ammonium chloride.

Superfatting Agents

Superfatting agents which can be used are substances such as, for example, lanolin and lecithin, and also polyethoxylated or acylated lanolin and lecithin derivatives, polyol fatty acid esters, monoglycerides and fatty acid alkanolamides, the latter simultaneously serving as foam stabilizers.

Stabilizers

Stabilizers which can be used are metal salts of fatty acids, such as e.g. magnesium, aluminum and/or zinc stearate or ricinoleate.

Polymers

Suitable cationic polymers are, for example, cationic cellulose derivatives, such as e.g. a quaternized hydroxyethylcellulose, which is available under the name Polymer JR 400® from Amerchol, cationic starch, copolymers of diallylammonium salts and acrylamides, quaternized vinylpyrrolidone/vinylimidazole polymers, such as e.g. Luviquat® (BASF), condensation products of polyglycols and amines, quaternized collagen polypeptides, such as, for example, lauryldimonium hydroxypropyl hydrolyzed collagen (Lamequat®L/Grunau), quaternized wheat polypeptides, polyethyleneimine, cationic silicone polymers, such as e.g. amodimethicones, co-polymers of adipic acid and dimethylaminohydroxypropyldiethylenetriamine (Cartaretins®/Sandoz), copolymers of acrylic acid with dimethyldiallylammonium chloride (Merquat® 550/Chemviron), polyaminopolyamides, and crosslinked water-soluble polymers thereof, cationic chitin derivatives such as, for example, quaternized chitosan, optionally in microcrystalline distribution, condensation products of dihaloalkylene, such as e.g. dibromobutane with bisdialkylamines, such as e.g. bis-dimethylamino-1,3-propane, cationic guar gum, such as e.g. Jaguar® CBS, Jaguar® C-17, Jaguar® C-16 from Celanese, quaternized ammonium salt polymers, such as e.g. Mirapol® A-15, Mirapol® AD-1, Mirapol® AZ-1 from Miranol.

Suitable anionic, zwitterionic, amphoteric and nonionic polymers are, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octylacrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinylcaprolactam terpolymers, and optionally derivatized cellulose ethers and silicones.

Biogenic Active Ingredients

Biogenic active ingredients are to be understood, for example, as meaning tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as e.g. prune extract, bambara nut extract and vitamin complexes.

Film Formers

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and/or salts thereof and similar compounds.

Antidandruff Active Ingredients

Suitable antidandruff active ingredients are piroctone olamine (1-hydroxy-4-methyl-6-(2,4,4-trimethylpentyl)-2-(1H)-pyridinone monoethanolamine salt), Baypival® (Climbazole), Ketoconazol®, ketoconazol, elubiol, selenium disulfide, sulfur colloidal, sulfur polyethylene glycol sorbitan monooleate, sulfur ricinol polyethoxylate, sulfur tar distillates, salicylic acid (or in combination with hexachlorophene), undexylenic acid monoethanolamide sulfosuccinate Na salt, Lamepon® UD (protein-undecylenic acid condensate), zink pyrithione, aluminum pyrithione and magnesium pyrithione/dipyrithione-magnesium sulfate.

Hydrotropes

To improve the flow behavior, hydrotropes, such as, for example, ethanol, isopropyl alcohol, or polios can also be used. Polios which are suitable here have preferably 2 to 15 carbon atoms and at least two hydroxyl groups. The polyols can also contain further functional groups, in particular amino groups, and/or be modified with nitrogen. Typical examples are glycerol;
alkylene glycols, such as, for example, ethylene glycol, diethylene glycol, propylene glycol, butylene glycol, hexylene glycol, and polyethylene glycols with an average molecular weight of from 100 to 1,000 Daltons;
technical-grade oligoglycerol mixtures with a degree of self-condensation of from 1.5 to 10, such as, for example, technical-grade diglycerol mixtures with a diglycerol content of from 40 to 50% by weight;
methylol compounds, such as, in particular, trimethylolethane, trimethylolpropane, trimethylolbutane, pentaerythritol and dipentaerythritol;
lower alkyl glucosides, in particular those having 1 to 8 carbon atoms in the alkyl radical, such as, for example, methyl glucoside and butyl glucoside;
sugar alcohols having 5 to 12 carbon atoms, such as, for example, sorbitol or mannitol,
sugars having 5 to 12 carbon atoms, such as, for example, glucose or sucrose;
amino sugars, such as, for example, glucamine;
dialcoholamines, such as diethanolamine or 2-amino-1,3-propanediol.

The total fraction of the auxiliaries and additives can be 1 to 50, preferably 5 to 40, % by weight, based on the compositions. The compositions can be produced by customary low-temperature or high-temperature processes; preference is given to working according to the phase inversion temperature method.

The present invention further provides the use of esters of fatty acids having 4 to 12 carbon atoms with pentaerythritol for increasing the deposition of silicones from conditioning cosmetic preparations on the hair. Preferably, fatty acids having 6 to 10 carbon atoms in the acyl radical are used.

EXAMPLES

In order to demonstrate the effectiveness of the preparations according to the invention, hair tresses were treated with it and the amount of silicone deposited on the hair was quantified.

Treatment of Hair Tresses

Five hair tresses per formulation to be tested were pre-cleaned by washing them with a 6% strength solution of Texapon NSO (6% active substance, sodium laureth sulfate, pH 6.5) and then thoroughly rinsing them. The cleaned hair tresses were bleached for 20 min with hydrogen peroxide (5% active substance, pH 9.4), followed by thorough rinsing and drying for one hour (stream of air at 55° C.). All of the described steps were carried out in an automatic system for preparing hair samples.

Treatment with Formulations 1-4

The five bleached hair tresses per formulation were wetted for one minute in an automatic rinsing and combing device. Then, 0.125 g of formulation/1 g of hair were applied to the wet hair tresses. After a contact time of three minutes, the hair tresses were rinsed for one minute in the automatic rinsing and combing device (at 38° C., 1 l/min for each hair tress). The hair tresses were dried for one hour with warm air (55° C.).

Analytical Determination of the Amount of Deposited Silicone

The amount of adsorbed silicone on the hair was determined with the help of ICP-OES analyses of extracts from the hair tresses. For this purpose, the hair was cut into pieces and the adsorbed silicone was extracted with o-xylene. The extracts were analyzed using a Vista MPX Radial (Varian Inc.) ICP instrument. The standard used was a certified polydimethylsiloxane (PDMS) calibration standard (Conostan®). The silicone concentration was calculated from the amounts of silicone multiplied by a factor (2.64) which was determined from the pure standard. This factor can also be used for modified silicones which the degree of derivatization is relatively low.

TABLE 1

Conditioners comprising silicones and pentaerythritol ester and amount of deposited silicone on hair

| Ingredients | 1 | 2 | 3 | 4 |
|---|---|---|---|---|
| Dehyquart BT (Behentrimonium chloride in ethanol) | 1.3 | 1.3 | 1.3 | 1.3 |
| Dehyquart B (Steartrimonium chloride in isopropanol) | 1.0 | 1.0 | 1.0 | 1.0 |
| Lanette O (Cetearyl alcohol) | 4.0 | 4.0 | 4.0 | 4.0 |
| Pentaerythritol dicaprylate | 1.0 | 3.0 | 1.0 | 3.0 |
| Cetiol OE (Dicaprylyl ether) | 1.0 | 1.0 | 1.0 | 1.0 |
| Gluadin WLM (Hydrolyzed wheat protein) | 1.0 | 1.0 | 1.0 | 1.0 |
| *Aloe vera* (*Aloe barbadensis* leaf extract) | 1.0 | 1.0 | 1.0 | 1.0 |
| Dimethicone* | 3.0 | 3.0 | | |
| Amodimethicone** | | | 3.0 | 3.0 |
| Glycerol | 2.0 | 2.0 | 2.0 | 2.0 |
| p-Paraben | | 0.15 | | |
| m-Paraben | | 0.15 | | |
| Water | | ad 100 | | |
| Silicone deposition [µg/g hair] | 304 | 289 | 320 | 305 |

*Dimethicone: SH200 200 cs (Dow)
**Amodimethicone: KF-8004 (ShinEtsu)

All example formulations lead to a high deposition of silicone on the hair.

The invention claimed is:

1. A cosmetic preparation comprising
   (a) esters of a fatty acid having 4 to 12 carbon atoms with pentaerythritol, wherein 5-35 wt % of the esters are monoesters, 20-50 wt % of the esters are diesters and 20-50 wt % of the esters are triesters, wherein the esters are esters of pentaerythritol with caprylic acid, and
   (b) a silicone.

2. The cosmetic preparation as claimed in claim 1, wherein component (b) comprises a dimethicone or amodimethicone.

3. The cosmetic preparation as claimed in claim 1, wherein the preparation further comprises quaternary ammonium compounds.

4. The cosmetic preparation as claimed in claim 1, wherein the preparation further comprises a wax or oil.

5. A method of increasing the deposition of silicones from conditioning cosmetic preparations onto hair, the method comprising contacting hair with a composition comprising esters of a fatty acid having 4 to 12 carbon atoms with pentaerythritol, wherein 5-35 wt % of the esters are monoesters, 20-50 wt % of the esters are diesters and 20-50 wt % of the esters are triesters; and a silicone.

6. The method as claimed in claim 5, wherein the esters comprise esters of pentaerythritol with caprylic acid.

7. The method as claimed in claim 5, e the silicone comprises a dimethicone or amodimethicone.

8. The method as claimed in claim 5, wherein the composition further comprises quaternary ammonium compounds.

9. The method as claimed in claim 5, wherein the composition further comprises a wax or oil.

10. The cosmetic preparation as claimed in claim 2, wherein the preparation further comprises quaternary ammonium compounds.

11. The cosmetic preparation as claimed in claim 2, wherein the preparation further comprises waxes and oils.

12. The cosmetic preparation as claimed in claim 3, wherein the preparation further comprises waxes and oils.

13. The cosmetic preparation as claimed in claim 1, wherein 5-11 wt % of the esters are tetraesters.

14. The method of claim 5, wherein 5-11 wt % of the esters are tetraesters.

* * * * *